US006228849B1

(12) United States Patent
Thys-Jacobs

(10) Patent No.: US 6,228,849 B1
(45) Date of Patent: May 8, 2001

(54) METHOD FOR TREATING SYMPTOMS ASSOCIATED WITH PREMENSTRUAL SYNDROME BY ADMINISTERING A COMBINATION OF CALCIUM AND VITAMIN D

(76) Inventor: Susan Thys-Jacobs, 135 Hickory Grove Dr., Larchmont, NY (US) 10538

( * ) Notice: Subject to any disclaimer, the term of this patent is extended or adjusted under 35 U.S.C. 154(b) by 0 days.

(21) Appl. No.: 08/059,682

(22) Filed: May 10, 1993

Related U.S. Application Data

(63) Continuation-in-part of application No. 07/945,319, filed on Sep. 15, 1992, now Pat. No. 5,354,743.

(51) Int. Cl.$^7$ .......................... A61K 31/59; A61K 33/06; A61K 33/10

(52) U.S. Cl. ...................... 514/167; 424/682; 424/686; 424/687

(58) Field of Search .................................. 424/682, 687, 424/686; 514/167, 168, 171, 899

(56) References Cited

U.S. PATENT DOCUMENTS

| | | | |
|---|---|---|---|
| 3,077,437 | 2/1963 | Heckel | 167/74 |
| 3,608,075 | 9/1971 | Glen et al. | 424/238 |
| 3,639,599 | 2/1972 | Mehrhof et al. | 424/239 |
| 4,035,504 | 7/1977 | Hidy et al. | 424/279 |
| 4,076,811 | 2/1978 | Lachnit-Fixson et al. | 424/239 |
| 4,145,416 | 3/1979 | Lachnit-Fixson et al. | 424/238 |
| 4,225,596 | 9/1980 | DeLuca | 514/167 |
| 4,241,087 | 12/1980 | Mir et al. | 424/324 |
| 4,252,797 | 2/1981 | Rosenthal | 424/201 |
| 4,291,028 | 9/1981 | Vorys | 424/238 |
| 4,315,033 | 2/1982 | Lawrason | 424/319 |
| 4,372,951 | 2/1983 | Vorys | 424/239 |
| 4,415,554 | 11/1983 | Horrobin | 424/145 |
| 4,439,432 | 3/1984 | Peat | 424/240 |
| 4,495,181 | 1/1985 | Norman et al. | 514/167 |
| 4,497,800 | 2/1985 | Larson et al. | 514/2 |
| 4,501,738 * | 2/1985 | Yamoto et al. | 514/167 |
| 4,521,410 | 6/1985 | Holick et al. | 514/26 |
| 4,542,026 | 9/1985 | Rios | 514/345 |
| 4,588,716 | 5/1986 | DeLuca et al. | 514/168 |
| 4,590,184 | 5/1986 | Macdo et al. | 514/167 |
| 4,650,668 | 3/1987 | Barron et al. | 424/44 |
| 4,738,856 | 4/1988 | Clark | 426/74 |
| 4,946,679 | 8/1990 | Thys-Jacobs | 424/682 |
| 5,037,823 | 8/1991 | Jones et al. | 514/222.8 |
| 5,063,221 | 11/1991 | Nishii et al. | 514/167 |
| 5,075,499 | 12/1991 | Walsdorf et al. | 562/590 |
| 5,104,864 * | 4/1992 | DeLuca et al. | 514/167 |
| 5,141,927 * | 8/1992 | Kroltkowski | 514/54 |

FOREIGN PATENT DOCUMENTS 2 169 202   7/1986   (GB).
2 254 556   10/1992  (GB).

OTHER PUBLICATIONS

Thys–Jacobs S. et al. Calcium supplementation in Premenstrual syndrome. A randomized crossover trial. J. Gen Int Med 1989; 4:183.
Chuong J. et al. Calcium levels in Premenstrual syndrome. Abstract presentation at The American Fertility Annual Meeting in 1991.
Nordin BEC, Peacock M, Aaron J et al. Osteoporosis and osteomalacia. Clin Endocrinol Metab 1980;9:177–205.
Frank RT. The hormonal causes of premenstrual tension. Arch Neurol Psyciatry. 1931;26:1503–7.
Reid RL. Premenstrual Syndrome. Am J Obstet Gynecol. 1981; 139:85–104.
Penland J. et al. Dietary calcium and manganese effects on menstrual cycle symptomatology. (1993—in press).
Barrett–Connor E. The RDA for calcium in the elderly: too little, too late. Calcif Tisue int 1989; 44:303.
Rubinow Dr. The Premenstrual Syndrome. JAMA, Oct. 14, 1992—vol. 268, No. 14, pp. 108–12.
Manoglas SC, et al. Metabolic Bone and Mineral Disorders. Churchill Livingstone (publisher), 1988, pp. 13–32.
Harrison M. "Self–Help for Premenstrual Syndrome," Random House, 3–5, 10–29, 75–77, 104–106 (1985).
Cummings, S. and Ullman, D., "Menstrual Cramps and Premenstrual Syndrome (PMS)", Everybody's Guide to Homeopathic Medicines, 149–150 (1991).
Seikus, P., "Vitamin Therapy Studied As PMS Treatment", Better Nutrition 50(2): 14–15 (1988).
Kendall, K. E. et al., "The Effects of Vitamin B6 Supplementation on Premenstrual Symptoms", Obstet. and Gynecol. 70(2): 145–149 (1987).
Sheikh, M.S. et al., "Gastrointestinal Absorption of Calcium From Milk and Calcium Salts", N. Engl. J. Med. 317:532–536 (1987).
Maddocks, S. et al., "A double–blind placebo–controlled trial of progesterone vaginal suppositories in the treatment of premenstrual syndrome", Am. J. Obstet., Gynecol, 154(3): 573–581 (1986).
Harrison, H., "Self–Help for Premenstrual Syndrome", Random House 1–5, 10–12, 25–28, 75–77, 104–106 (1985).
Price, W. A., et al., "Premenstrual Tension Syndrome", Resident and Staff Physician, 31(5): 35 (1985).
Muse, K. N., et al., "The Premenstrual Syndrome", N. Engl. J. Med. 311: 1345–1349 (1984).
Abraham, G. E., "Nutritional Factors in the Etiology of the Premenstrual Tension Syndromes", J. Reproductive Med., 28(7): 446–464 (1983).

(List continued on next page.)

*Primary Examiner*—Theodore J. Criares
(74) *Attorney, Agent, or Firm*—Gottlieb, Rackman & Reisman, P.C.

(57) ABSTRACT

The present invention is directed to a method for treating symptoms associated with premenstrual syndrome. The method comprises administering to an individual in need of treatment an amount of a combination of elemental calcium and vitamin D effective to reduce the symptoms associated with premenstrual syndrome.

21 Claims, No Drawings-

OTHER PUBLICATIONS

London, R. S., et al., "The Effect of β–Tocopherol on Premenstrual Symptomatology: A Double–Blind Study", J. An. Coll. Nutr., 2: 115–122 (1983).

Abraham, G. E., "Magnesium deficiency in prementrual tension", Magnesium Bull. 4: 68–72 (1982).

Reid, R. L., et al., "Premenstrual syndrome", Am. J. Obestet, Gynecol. 139(1): 86–97 (1981).

Handbook of Non–Prescription Drugs, 1979, 6th Edition, pp. 239–245.

Haynes, R. C. and Murad, F., "Agents Affecting Calcification: Calcium, Parathyroid Hormone, Calcitonin, Vitamin D and Other Compounds", Goodman and Gilman's The Pharmological Basis of Therapeutics, 6th Ed., Chapter 65 p. 1524–1529 (1980).

Argonz, J. and Abinzano, C., "Premenstrual Tension Treated With Vitamin A", J. Clin. Endocrinol. Metab. 10: 1579 (1950).

Zondek, B. and Brzezinski, A., "Inactivation of Oestrogenic Hormone By Women with Vitamin B Deficiency", Br., J. Obstet, Gynicol. 55: 273 (1948).

Greenhill, J.P., and Freed S.C., "The Electrolyte Therapy of Premenstrual Distress", JAMA 117: 504 (1941).

Israel, S. L., "Premenstrual Tension", JAMA 110: 721 (1938).

Frank, R.T., "The Hormonal Causes of Premenstrual Tension", Arch, Neurol. Psychiatr. 26: 1053 (1931).

Price, W.A. and Giannini, A.J., "Premenstrual Tension Syndrome", Resident and Staff Physician, 31(5):34–38 (1985).

* cited by examiner

METHOD FOR TREATING SYMPTOMS ASSOCIATED WITH PREMENSTRUAL SYNDROME BY ADMINISTERING A COMBINATION OF CALCIUM AND VITAMIN D

TECHNICAL FIELD

This is a continuation-in-part of application Ser. No. 07/945,319 filed Sep. 15, 1992, by the same inventor now U.S. Pat. No. 5,354,743.

BACKGROUND OF THE INVENTION

This invention relates to a method for reducing or relieving symptoms associated with premenstrual syndrome ("PMS") by administering to an individual exhibiting PMS symptomology a therapeutically effective amount of a combination of calcium and vitamin D.

BACKGROUND OF THE ART

Symptoms generally experienced by women with PMS, the occurrence and exaggeration of mood and behavioral disturbances in women during the latter half of their menstrual cycle, without limitation include (1) somatic symptoms such as abdominal cramps, headaches including vascular headaches such as migraine headaches, breast fullness and tenderness, back pain and bloating and (2) psychological symptoms such as, depression, irritability and anxiety. While these symptoms, which are among those generally related to PMS, do not occur solely in women with PMS, it has been estimated that as much as 90% of all premenopausal women exhibit some degree of symptoms such as those above related to PMS, ranging from mild to incapacitating, and that about 7 million women suffer severe and incapacitating symptoms related to PMS.

U.S. Pat. No. 4,946,679 of Thys-Jacobs and the article by Thys-Jacobs et al. entitled "Calcium Supplementation in Premenstrual Syndrome. A Randomized Crossover Trial", *J. Gen. Int. Med.*, 1989:4:183, showed that elemental calcium is effective in significantly reducing symptoms associated with PMS when administered, for example, in a daily dose of 1000 mg for 3 months. Thys-Jacobs et al. reported a 50% reduction in PMS symptomology for the daily administration of elemental calcium in the dose of 1000 mg for three months. Similarly, Chuong et al., in an abstract presented at the American Fertility Annual Meeting in 1991 entitled "Calcium Levels in Premenstrual Syndrome" showed that women with PMS had significantly lower calcium levels during the luteal phase of the menstrual cycle as compared with asymptomatic controls and also showed that women with PMS had significantly lower calcium levels during the luteal phase of the menstrual cycle as compared to the follicular phase of the menstrual cycle.

However, there still exists a need for therapy that provides further reduction or relief of symptoms associated with PMS, especially in particularly persistent cases.

SUMMARY OF THIS INVENTION

An object of this invention is to reduce or relieve symptoms associated with PMS in an individual exhibiting such symptoms, especially in those patients who do not demonstrate improvement when treated with calcium alone.

The present invention is directed to a method of at least reducing symptoms associated with PMS. A therapeutically effective amount of a combination of calcium and vitamin D is administered to an individual exhibiting symptomatology associated with PMS.

DETAILED DESCRIPTION OF THE INVENTION

The method of the present invention treats individuals exhibiting symptoms associated with PMS by the administration of a therapeutically effective amount of a combination of calcium and vitamin D. Preferably, the dosage of elemental calcium administered is in the range of from about 1000 mg to about 2000 mg per day. Preferably, the dosage of vitamin D administered is in the range of from about 400 to about 2000 IU per day. Preferably, the dosage of vitamin D elevates 25 hydroxyvitamin D levels to levels greater than 30–40 ng/ml. The calcium and vitamin D may be administered concurrently such as, for example, by administration of a tablet, a capsule, a powder, liquid, candy or mint, cookie or food additive containing the desired dosages of the calcium and the vitamin D. Preferably, the combination is administered orally in the form of a tablet. Calcium may be administered in the form of calcium carbonate, calcium gluconate, calcium citrate, calcium phosphate, calcium chloride, calcium stearate or calcium acetate, and preferably in the form of calcium carbonate. Vitamin D may be administered as at least one of vitamin $D_2$ (ergocalciferol), vitamin $D_3$ (cholecalciferol) or 25 hydroxyvitamin D (calcidiol or calcifediol). The dose can be taken as a single daily combination dose or in split doses of smaller concentrations in adequate levels for prevention of PMS symptoms. Examples of combinations for single doses are as follows:

| Elemental calcium | Vitamin $D_2$ or $D_3$ |
| --- | --- |
| 1000 mg | 400 IU |
| 1000 mg | 600 IU |
| 1000 mg | 800 IU |
| 1200 mg | 400 IU |
| 1200 mg | 600 IU |
| 1200 mg | 800 IU |
| 1200 mg | 1000 IU |
| 1200 mg | 1200 IU |
| 1500 mg | 400 IU |
| 1500 mg | 300 IU |
| 1500 mg | 800 IU |
| 1500 mg | 1000 IU |
| 1500 mg | 1200 IU |
| 1500 mg | 2000 IU |

Examples of smaller concentration embodiments to be administered at least 2 to 3 times daily are as follows:

| Elemental calcium | Vitamin $D_2$ or $D_3$ |
| --- | --- |
| 300 mg | 200 IU |
| 300 mg | 250 IU |
| 500 mg | 200 IU |
| 500 mg | 300 IU |
| 500 mg | 400 IU |
| 600 mg | 300 IU |
| 600 mg | 400 IU |
| 600 mg | 500 IU |
| 600 mg | 600 IU |
| 700 mg | 700 IU |
| 800 mg | 400 IU |
| 800 mg | 800 IU |
| 800 mg | 800 IU |
| 2000 mg | 2000 IU |

The combination is effective for reducing or relieving symptoms associated with PMS, which include somatic symptoms such as without limitation headaches, especially vascular headaches such as migraine headaches, tenderness and swelling of the breasts, abdominal bloating, abdominal cramping, generalized aches and pains, lower backache, fatigue, increased/decreased appetite, craving for sweet/salt, swelling or edema of extremities and insomnia and which include psychological symptoms such as mood swings, depression, tension, anxiety, anger and crying spells.

The foregoing and other objects, features, aspects and advantages of the present invention will become more apparent from the following detailed non-limiting examples of the present invention.

EXAMPLE 1

Applicant's Research Study Indicating That Many Women With PMS Have A Vitamin D Deficiency 1.1 Enrollment of Participants The study herein described was conducted at Mount Sinai Hospital in New York City. Women working and residing in the New York area with a self-diagnosis of PMS were recruited.

From those women reporting a self-diagnosis of PMS, women were further selected if they fulfilled a strict definition of premenstrual syndrome: Cyclically recurring symptoms during the luteal phase of the menstrual cycle which subside with the onset of menstruation. Determination of recurrence of symptoms was based on a prospective and consecutive two month daily diary. Each woman was asked to complete daily pre-trial self-assessment questionnaires where 17 symptoms were measured and recorded daily over one menstrual cycle. Each was instructed to complete one questionnaire every evening, describing how she felt during the previous 24 hours by recording her level of symptom severity for each of the seventeen symptoms. The 17 symptoms evaluated were: mood swings, depression, tension, anxiety, anger, crying spells, tenderness and swelling of breasts, abdominal bloating, abdominal cramping, generalized aches and pains, low backache, headache, fatigue, increased/decreased appetite, cravings for sweet/ salt, swelling/edema of extremities and insomnia. Each symptom was marked daily on a four-point scale (absent, mild, moderate, severe) and subsequently scored from 0 to 3. Women were further selected if their mean symptom scores from the latter seven days of the luteal phase were at least 50% greater than the seven days following the days of menstruation.

Criteria for exclusion from the clinical trial were: (1) history of renal disease, (2) history of primary hyperparathyroidism, (3) history of liver or gastrointestinal disease, (4) history of endometriosis, (5) history of psychosis and (6) active depression.

22 women were finally selected for this study. A preliminary evaluation on each finally selected woman ("patient") included (1) a standardized medical evaluation with a detailed gynecological history as well as a routine physical examination and (2) a determination of complete blood count, electrolytes, alkaline phosphatase, albumin, glucose and urinalysis. All determinations of the above were within normal laboratory limits as set by the laboratory performing the determinations.

1.2 Study

For all women baseline levels for calciotropic hormones 1,25 dihydroxyvitamin D [1,25(OH)$_2$D], 25 hydroxyvitamin D [25OHD] and intact parathyroid hormone (iPTH) were determined at the midpoint in the menstrual cycle. Additionally, baseline calcium levels were determined at the midpoint in the menstrual cycle. All determinations and evaluations of serum samples were performed by a single central laboratory, Nichols Institute of California.

Serum samples for the 1,25(OH)$_2$D assay were extracted with acetonitrile and purified by Sep-pak C-18 and Sep-Pak silica columns. The purified 1,25(OH)$_2$D was assayed in a radioreceptor assay using calf thymus and $_3$H-1,25(OH)$_2$D.

The serum samples for the 25OHD assay, like the 1,25 (OH)$_2$D samples, were extracted with acetonitrile and purified through C-18 Sep-Pak columns. The purified 25OHD sample was assayed in a radiobinding assay using $_3$H-25OHD and rat serum binding protein.

The intact parathyroid hormone assay is a two site immunoradiometric assay (IRMA). The IRMA employs two kinds of anti sera, one is specific to the C-terminal portion of the molecule and the other is specific to the N-terminal end. The assay measures only the intact hormone.

The serum samples for total calcium were assayed by atomic absorption spectrometry.

The results are shown below in Table 1. Normal values for the calciotropic hormones 1,25(OH)$_2$D, 25OHD and intact parathyroid hormone (iPTH) and calcium are shown below in Table 2.

TABLE 1

CALCIOTROPIC HORMONES IN WOMEN WITH PREMENSTRUAL SYNDROME

| Patient | Cycle Day | 25OHD ng/ml | T.calcium mg/dl | iPTH pg/ml | 1,25(OH)$_2$D pg/ml |
|---|---|---|---|---|---|
| 001 | 14 | 18 | 9.6 | 71 | 46 |
| 002 | 12 | 17 | 9.6 | 46 | 60 |
| 003 | 15 | 20 | 8.7 | 70 | 38 |
| 004 | 13 | 24 | 9.5 | 25 | 51 |
| 005 | 12 | 17 | 9.1 | 68 | <5 |
| 006 | 15 | 16 | 9.6 | 49 | 52 |
| 007 | 15 | 16 | 8.8 | 30 | 69 |
| 008 | 13 | 17 | 8.9 | 86 | 75 |
| 009 | 17 | 27 | 9.3 | 61 | 57 |
| 010 | 16 | 24 | 8.9 | 60 | 36 |
| 011 | 13 | 33 | 9.4 | 54 | 46 |
| 012 | 14 | 25 | 9.4 | 50 | 46 |
| 013 | 14 | 19 | 9.4 | 65 | 44 |
| 014 | 15 | 27 | 9.8 | 66 | 50 |
| 015 | 13 | 21 | 9.3 | 47 | 84 |
| 016 | 13 | 27 | 10.0 | 26 | 40 |
| 017 | 15 | 23 | 9.0 | 21 | 21 |
| 018 | 14 | 27 | 9.6 | 31 | 51 |
| 019 | 14 | 35 | 9.3 | 39 | 63 |
| 020 | 14 | 24 | 9.3 | 21 | 54 |
| 021 | 15 | 21 | 8.9 | 48 | 15 |
| 022 | 15 | 21 | 9.0 | 32 | 32 |

Cycle day refers to the day of the menstrual cycle when the serum sample was drawn.
T.calcium refers to total calcium.

TABLE 2

NORMAL CALCIOTROPIC HORMONE VALUES AS DETERMINED BY LABORATORY

|  | 25OHD ng/ml | T.calcium mg/dl | iPTH pg/ml | 1,25(OH)$_2$D pg/ml |
|---|---|---|---|---|
| Normal Values | 9–52 | 8.8–10.4 | 10–65 | 15–60 |

1.3 Discussion of Lab Results

Only one patient was determined to be hypocalcemic. Five women were determined to have elevated iPTH determinations, while five were determined to have abnormal 1,25(OH)$_2$D levels with four elevated and one undetectable. All were determined to have normal 25OHD levels. Thus, a total of ten women were determined to have abnormally elevated iPTH or 1,25(OH)$_2$D determinations when these measurements were drawn at the midpoint of the menstrual cycle. It has been mentioned by Nordin et al. in an article entitled "Osteoporosis and Osteomalacia" in *Clin. Endocrinal Metab.*, 1980; 9; 177–205 that a raised iPTH level might indicate a vitamin D deficiency. Five women were determined to have elevated iPTH levels and might be considered vitamin D deficient. However, elevated iPTH is a necessary but not a sufficient condition to absolutely diagnose a vitamin D deficiency.

1.4 Treatment

Each woman was instructed to take daily supplementation with 600 to 2000 IU per day of vitamin D$_2$ or D$_3$ and 1200 mg to 1500 mg per day of elemental calcium.

1.5 Results

Daily supplementation with vitamin D in doses of 600 to 2000 IU per day and with elemental calcium in doses of 1200 mg to 1500 mg per day resulted in a significant relief of PMS symptomology. Within months this therapy resulted in an elevation of the 25OHD level above 30–40 ng/ml, and for those women with abnormal calciotropic values as defined by the laboratory, such values were corrected to within normal determinations. To prevent recurrence each was instructed to continue lifetime vitamin D and calcium supplementation.

EXAMPLE 2

Case Studies Applying Applicant's Research Finding 2.1 Patient X

Patient X is a 47 year old female with a 20 year history of PMS. Her major symptoms included severe irritability, mood swings, breast swelling and tenderness, and menstrual cramps. Vascular headaches, specifically common migraines (or migraines without aura), frequently interfered with her functional well being during both the premenstrual and menstrual phases of her menstrual cycle. She occasionally suffered with classic migraines (or migraines with aura) at least 4 to 5 times a year. Her common migraines were characterized by a pulsating quality of severe intensity lasting 2–3 days, associated with photophobia, nausea, occasional vomiting, and exacerbated by routine physical activity. These migraines were temporally related to the onset of her menstrual period and were always associated with her PMS symtomatology. Her past medical history was significant for mild hypertension, polycystic kidney disease, mitral valve prolapse with mitral regurgitation, recurrent vaginitis, and amenorrhea 22 years ago. She had a very strong family history of breast cancer with a mother, aunt and sister all diagnosed with cancer. She is at major risk for the development of breast cancer with such a strong family history of breast cancer, a personal history of cyclical mastopathy, and a residence in the New England region. She requires an annual mammogram and breast examination for cancer screening.

Calciotropic hormone levels in this patient:
4/92: total calcium 8.5 mg/dl (8.6–10.1)
  iPTH—8.5 pmol/L (1.0–6.8)
  25OHD—14 mcg/L (10–80)
  1,25(OH)$_2$D—30.3 ng/L (18.0–62.0)
7/92: total calcium 9.10 mg/dl (8.6–10.1)
11/92: total calcium 9.00 mg/dl (8.6–10.1)
  iPTH—7.3 pmol/L (1.0–6.8)
  25OHD—30.3 mcg/L (10.0–80.0)
  1,25(OH)$_2$D—50.1 ng/L (18.0–62.0)
2/93: total calcium 9.70 mg/dl (8.6–10.1)
  iPTH—4.30 pmol/L (1.0–6.8)
  25OHD—34.5 mcg/L (10–80)

She was diagnosed with PMS by history, by prospective charting of symptoms and by a luteal to intermenstrual ratio of greater than 150%. Laboratory results confirmed hypocalcemia with a secondary hyperparathyroidism and a normal 25OHD. In 4/92, she was treated with elemental calcium in the dose of 1200 mg/day and continued on her daily multivitamins (which included a low dose of elemental calcium and the RDA for vitamin D). Over the next 2 months, this resulted in complete correction of her hypocalcemia, but only partial relief of her premenstrual irritability and menstrual cramps. She was then prescribed 400 additional IU of cholecalciferol, while elemental calcium was increased to 1500 mg per day. Her vascular headaches persisted, and she still complained of nocturnal menstrual cramps. In 11/92, her total calcium was normal, her iPTH was elevated and her 25OHD remained normal as defined by the laboratory. She was prescribed 1000 IU of cholecalciferol per day and maintained on 1500 mg of elemental calcium per day in addition to her daily multivitamin (total vitamin D intake therefore amounted to 1200 IU). On this regimen, her iPTH normalized, her 25OHD increased to 34.5 mcg/L and her symptoms resolved. In addition, her blood pressure normalized. By recommending appropriate doses of vitamin D and calcium, and maintaining the 25OHD level above 35.0 mcg/L with semiannual determinations, symptomatology was prevented.

2.2 Patient Y

Y is a 47 year old female with a history of Rheumatic fever, mild hypertension and a 30 year history of PMS. She presented with severe premenstrual and menstrual symptomatology occurring 10 to 14 days prior to the onset of her menstrual period. Her symptoms consisted of anxiety, extreme nervousness, breast tenderness and fullness, abdominal bloating, body aches, lack of energy, vascular headaches, and severe menstrual cramps. Her symptoms were of such severity that her co-workers at her job ostracized her, and criticized her monthly abnormal behavior. With prospective charting of the daily symptoms described in Example 1.1 (less insomnia) over two menstrual cycles, PMS was confirmed. Her luteal mean score was 48 (the maximum achievable score). Baseline total calcium was 9.9 ng/ml (8.8–10.4), 25OHD was 24 ng/ml (9–52) and iPTH was 54 pg/ml (10–65). Laboratory determinations showed that she had a serum calcium that was normal as defined by the laboratory, a vitamin D level that was normal, and a iPTH that was normal. Prescribed daily treatment with 1200 mg of elemental calcium and 800 IU of cholecalciferol completely resolved her headaches, abdominal cramps, irritability, lethargy, breast tenderness/fullness, and behavioral changes.

The present invention is not to be limited in scope by the embodiments disclosed in the examples which are intended as illustrations of aspects of the invention. Any methods which are functionally equivalent are within the scope of this invention. Indeed, various modifications of the invention in addition to those shown and described herein will become apparent to those skilled in the art from the foregoing description. Such modifications are intended to fall within the scope of the appended claims.

I claim:

1. A method for treating premenstrual syndrome comprising periodically administering to an individual having premenstrual syndrome symptomatology synergistic effective amounts of a combination of calcium and vitamin D effective to significantly reduce said symptomatology.

2. The method of claim 1 which further comprises administering calcium in the form of calcium carbonate.

3. The method of claim 1 which further comprises administering vitamin D in the form of ergocalciferol, cholecalciferol or calcifediol.

4. The method of claim 1 which further comprises administering the combination orally in the form of a tablet in a single daily dose.

5. A method for treating premenstrual syndrome comprising periodically administering to an individual having premenstrual syndrome symptomatology synergistic effective amounts of a combination of calcium in the range of from about 1000 mg to about 2000 mg per day and vitamin D effective to significantly reduce said symptomatology.

6. The method of claim 5 which further comprises administering vitamin D in the range of from about 400 to about 2000 IU per day.

7. A method for treating premenstrual syndrome comprising periodically administering to an individual having premenstrual syndrome symptomatology synergistic effective amounts of a combination of calcium and vitamin D effective to significantly reduce said symptomatology, which further comprises administering the combination orally in the form of a tablet in daily doses and which further comprises administering said calcium in the range of from about 1000 mg to about 2000 mg per day.

8. A method for treating premenstrual syndrome comprising periodically administering to an individual having premenstrual syndrome symptomatology synergistic effective amounts of a combination of calcium and vitamin D effective to significantly reduce said symptomatology, which further comprises administering said calcium orally in the form of a tablet in daily doses in an amount of about 1200 mg per day and vitamin D in an amount of about 1000 IU per day.

9. A method for treating premenstrual syndrome comprising periodically administering to an individual having premenstrual syndrome symptomatology synergistic effective amounts of a combination of calcium and vitamin D effective to significantly reduce said symptomatology, which further comprises administering vitamin D in an amount effective to elevate the individuals 25 hydroxyvitamin D level to a level greater than 30–40 ng/ml.

10. The method of claim 7 which further comprises administering vitamin D in an amount effective to elevate the individual's 25 hydroxyvitamin D level to a level greater than 30–40 ng/ml.

11. The method of claim 1 further comprising administering the combination to an individual whose symptomatology includes vascular headaches to at least reduce vascular headaches.

12. A method for treating premenstrual syndrome comprising periodically administering to an individual having premenstrual syndrome symptomatology synergistic effective amounts of a combination of calcium and vitamin D effective to significantly reduce said symptomatology which further comprises administering calcium and vitamin D in a 1:1 ratio.

13. A method for treating premenstrual syndrome comprising periodically administering to an individual having premenstrual syndrome symptomatology and a 25 hydroxyvitamin level less than 30 ng/ml synergistic effective amounts of a combination of calcium and vitamin D effective to elevate the individual's 25 hydroxyvitamin D level to a level greater than 30–40 ng/ml and to significantly reduce said symptomatology.

14. The method of claim 13 which further comprises administering calcium in the form of calcium carbonate.

15. The method of claim 13 which further comprises administering vitamin D in the form of 15 ergocalciferol, cholecalciferol or calcifediol.

16. The method of claim 13 which further comprises administering the combination orally in the form of a tablet in a single daily dose.

17. The method for treating premenstrual syndrome of claim 13 wherein the calcium administered is in the range of from about 1000 mg to about 2000 mg per day.

18. The method for treating premenstrual syndrome of claim 17 wherein the vitamin D is administered in the range of from about 400 to about 2000 IU per day.

19. The method for treating premenstrual syndrome of claim 13 wherein the combination of calcium and vitamin D is administered orally in the form of a tablet in a single daily dose and in which said calcium is in the range of from about 1000 mg to about 2000 mg per day.

20. The method for treating premenstrual syndrome of claim 13 wherein said calcium is administered orally in the form of a tablet in a single daily dose in an amount of about 1200 mg per day and vitamin D in an amount of about 1000 IU per day.

21. The method for treating premenstrual syndrome of claim 13 wherein the calcium and vitamin D are administered in a 1:1 ratio.

* * * * *